United States Patent [19]

Jarreau et al.

[11] Patent Number: 4,526,895

[45] Date of Patent: Jul. 2, 1985

[54] 3-PYRIDYL-5-ALKOXY-PYRAZOLE DERIVATIVES AND PHARMACEUTICAL COMPOSITION FOR USE AS A CARDIOTONIC MEDICATION

[75] Inventors: Francois-Xavier Jarreau, Versailles; Jean-Jacques Koenig, Vernou la Celle, both of France

[73] Assignee: Etablissements NATIVELLE S.A., Paris, France

[21] Appl. No.: 513,190

[22] Filed: Jul. 12, 1983

[30] Foreign Application Priority Data

Jul. 12, 1982 [FR] France ................ 82 12176

[51] Int. Cl.³ ............... A61K 31/44; C07D 401/04
[52] U.S. Cl. ................... 514/341; 546/279
[58] Field of Search ............ 546/279; 424/263

[56] References Cited

FOREIGN PATENT DOCUMENTS 2167997 1/1973 France .
2327779 10/1976 France .
2470124 11/1980 France .
2477148 2/1981 France .
2481284 4/1981 France .

Primary Examiner—Jane T. Fan
Attorney, Agent, or Firm—Sughrue, Mion, Zinn, Macpeak, and Seas

[57] ABSTRACT

The invention relates to new 3-pyridyl-5-alkoxy-pyrazole derivatives of the following formula:

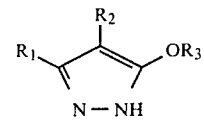

wherein $R_1$ represents a 4-pyridyl, 3-pyridyl or 2-pyridyl group which is unsubstituted or which may be substituted with one or two lower alkyl groups; $R_2$ represents a hydrogen atom or a lower alkyl group; and $R_3$ represents a lower alkyl group, a phenyl group or an aralkyl group; and the acid addition salts thereof. The derivatives may be prepared by alkylation of a 3-pyridyl-5-pyrazolone. The derivatives are medicinally useful, particularly for the treatment of cardiac deficiency.

10 Claims, No Drawings

3-PYRIDYL-5-ALKOXY-PYRAZOLE DERIVATIVES AND PHARMACEUTICAL COMPOSITION FOR USE AS A CARDIOTONIC MEDICATION

FIELD OF THE INVENTION

The present invention relates to new pyrazole derivatives, and in particular to new 3-pyridyl-5-alkoxy-pyrazole derivatives, a process for their preparation, and their medicinal use.

BACKGROUND OF THE INVENTION

In the field of medicinal compounds, various derivatives of pyridinone or pyridazinone substituted with a pyridyl group are known, for example, 5-pyridyl-2-pyridinones as in French Pat. Nos. 2,327,779, 2,470,124 and 2,477,148, or 6-(pyridyl-4')-(2H)-3-pyridazinones as in French Pat. No. 2,481,284. These compounds have the property of increasing cardiac contractility and may be used as cardiotonic medications. On the other hand, no comparable pyrazole derivatives with such properties are known.

In addition, French Pat. No. 2,167,997 describes 1-amino-5-pyrazolone and 1-amino-5-methoxy pyrazole derivatives having a depressant activity on the central nervous system.

SUMMARY OF THE INVENTION

The work undertaken by applicants has shown that certain 5-alkoxy-pyrazole derivatives, substituted at the 3-position with a pyridyl group, possess interesting inotropic properties enabling their medicinal use as cardiotonic medications.

Accordingly, one object of the present invention is to provide new 3-pyridyl-5-alkoxy-pyrazole derivatives, as well as a process for the preparation of these compounds.

A further object of the present invention is to provide pharmaceutical compositions containing, as active constituents, 3-pyridyl-5-alkoxy-pyrazole derivatives, such compositions being particularly useful as cardiotonic agents.

These objects are achieved in the present invention by a new 3-pyridyl-5-alkoxy-pyrazole derivative represented by the following general formula (I):

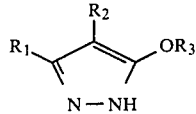
(I)

wherein $R_1$ represents a 4-pyridyl, 3-pyridyl or 2-pyridyl group which is unsubstituted or which may be substituted with one or two lower alkyl groups; $R_2$ represents a hydrogen atom or a lower alkyl group; and $R_3$ represents a lower alkyl group, a phenyl group or an aralkyl group; and the acid addition salts thereof.

DETAILED DESCRIPTION OF THE INVENTION

As stated above, the present invention relates to new 3-pyridyl-5-alkoxy-pyrazole derivatives in accordance with the present invention may be represented by general formula (I) below:

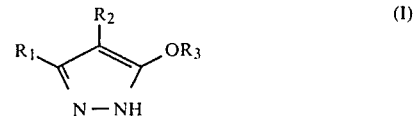
(I)

wherein $R_1$ represents a 4-pyridyl, 3-pyridyl or 2-pyridyl group which may be unsubstituted or substituted with one or two lower alkyl groups; $R_2$ represents a hydrogen atom or a lower alkyl group; and $R_3$ represents a lower alkyl group, a phenyl group or an aralkyl group.

The expression "lower alkyl group" means a linear or branched alkyl group containing 1 to 4 carbon atoms, such as a methyl, ethyl, n-propyl, isopropyl group, etc.

When substituted with a lower alkyl group, the pyridyl group can be, for example a 2-methyl-4-pyridyl, 4-methyl-2-pyridyl, 2,6-dimethyl-4-pyridyl, 2-ethyl-4-pyridyl, 2-isopropyl-4-pyridyl, 2,6-dimethyl-3-pyridyl group, etc.

The invention preferably relates to the 3-pyridyl-5-alkoxy pyrazoles of the general formula (I) above wherein $R_1$ is a 4-pyridyl, 3-pyridyl or 2-pyridyl group, $R_2$ is a hydrogen atom or a methyl group, and $R_3$ is a methyl, ethyl, isopropyl, phenyl or benzyl group.

The compounds of general formula (I) may exist under several equilibrium forms shown below:

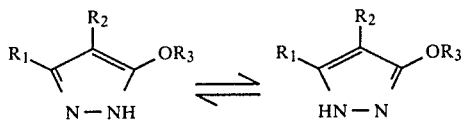

The invention also relates to the various equilibrium forms of said compounds.

The invention also extends to the 3-pyridyl-5-alkoxy-pyrazole salts of general formula (I) and in particular to the pharmaceutically acceptable salts obtained by action of a mineral or organic acid in accordance with the conventional methods of the art. The acid used may be selected from among hydrochloric acid, sulfuric acid, oxalic acid, tartaric acid, fumaric acid, lactic acid, citric acid, phosphoric acid, p-toluene sulfonic acid, formic acid, hydrobromic acid, maleic acid, sulfamic acid, etc.

The 3-pyridyl-5-alkoxy-pyrazoles of general formula (I) can be prepared in accordance with the invention by reacting, in a suitable organic solvent, an alkylation agent with 3-pyridyl-5-pyrazolone of the general formula (II):

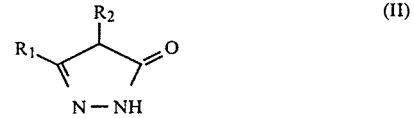
(II)

wherein $R_1$ and $R_2$ have the same meaning as in formula (I).

The alkylation is carried out in solution, at ambient temperature, by means of an 0-alkylation agent, for example diazomethane.

The solvent can, for example, be benzene, toluene, an alcohol such as methanol, ethanol or isopropanol, an ether such as dimethyl ether, diethyl ether, dioxane, tetrahydrofuran, etc., separately or in a mixture.

It is preferable to carry out the alkylation reaction of the 3-pyridyl-5-pyrazolone of formula (II) with an alcohol activated by means of triphenylphosphine and ethyl azodicarboxylate in a neutral medium, by use of the method of O. Mitsunobu (*Synthesis,* (1981) page 1). This alkylation reaction is carried out by adding triphenylphosphine to a mixture of 3-pyridyl-5-pyrazolone of formula (II), alcohol and ethyl azodicarboxylate in an aprotic solvent such as tetrahydrofuran, dimethylformamide or an aromatic hydrocarbon, at a temperature of between 0° and 20° C. The alkylation reaction may also be carried out in converse by adding ethyl azodicarboxylate to a mixture of 3-pyridyl-5-pyrazolone, alcohol and triphenylphosphine. In a third method of carrying out the alkylation reaction, 3-pyridyl-5-pyrazolone and alcohol may be added to a mixture of triphenylphosphine and ethyl azodicarboxylate previously cooled to a temperature of between −20° and −10° C.

The alcohol used for this reaction is selected in accordance with the substituent which it is desired to graft onto the oxygen atom of the pyrazolone nucleus, and can be represented by the formula $R_3$—OH where $R_3$ is defined as above. For example, methanol, ethanol, isopropanol, etc., may be used.

Certain of the 3-pyridyl-5-pyrazolones of general formula (II) are known products, for example 3-(4-pyridyl)-5-pyrazolone is described by H. L. Yale et. al., *JACS,* 75, p. 1933 (1953). In accordance with Yale et. al., 3-(4-pyridyl)-5-pyrazolone can be prepared by reacting hydrazine hydrate with ethyl isonicotinyl-acetate in n-propanol. Similarly, the compounds of formula (II) can be prepared by reacting by a cyclization reaction in an acid medium, hydrazine hydrate with a ketoester of general formula (III)

$$R_1-CO-CHR_2-COOC_2H_5 \qquad (III)$$

where $R_1$ and $R_2$ have the definitions given above.

The following examples illustrate the invention without limiting the scope thereof. The structures of the derivatives have been confirmed by analysis and IR and NMR spectra.

EXAMPLE 1

3-(4-pyridyl)-5-methoxy-pyrazole 300 ml of a solution of approximately 0.5N diazomethane in diethyl ether, freshly prepared, were gradually poured into a 1 liter flask containing 16.1 g of 3-(4-pyridyl)-5-pyrazolone in 150 ml of cold methanol under agitation.

The reaction was allowed to take place for 24 hours at room temperature. The solvent was then evaporated until the contents were dry. The residue was dissolved in 50 ml of chloroform, and the solution was filtered to eliminate the remaining quantity of starting pyrazolone which was not reacted. The chloroform phase was then extracted with diluted sodium hydroxide. Diluted hydrochloric acid was added to the aqueous phase to bring the pH to 4, the solution was extracted with chloroform, and then crystallization was carried out in diisopropyl ether.

In this manner, 9.1 g (yield 52%) of 3-(4-pyridyl)-5-methoxy pyrazole was obtained with the following characteristics:

Melting point M.P.=140° C.

IR spectrum (Nujol) ν=3500 to 2200, 1610 1575, 1550, 1520, 1400, 1040 cm$^{-1}$

NMR spectrum δ=3.9 (s,3H), 6.4 (s,1H), 7.7 (2H), 8.6 (2H), 12.7 (1H mobile) ppm (DMSOd$_6$).

The starting pyrazolone, recuperated by filtration of the chloroform solution, can be recycled to improve the yield.

HYDROCHLORIDE

To a solution of 50 ml of isopropanol containing 5 g of 3-(4-pyridyl)-5-methoxy pyrazole, concentrated hydrochloric acid was added slowly until the pH was approximately 2 to 3. The hydrochloride crystals were precipitated and collected by filtration (yield 95%).

Melting point M.P.=205° C.

EXAMPLE 2

3-(4-pyridyl)-4-methyl-5-methoxy-pyrazole 1.5 mg of 3-(4-pyridyl)-4-methyl-5-pyrazolone, 2.3 g of triphenylphosphine and 0.27 g of methanol were placed in 30 ml of tetrahydrofuran. The mixture was cooled on an ice bath to 2° C. and 1.6 g of ethyl azodicarboxylate dissolved in 9 ml of tetrahydrofuran was added dropwise.

After the addition, the reaction medium was allowed to return to room temperature, then after 4 hours the insoluble material was filtered. Concentrated hydrochloric acid was added under agitation and the 3-(4-pyridyl)-4-methyl-5-methoxy pyrazole hydrochloride was filtered and purified by crystallization in methanol.

Melting point M.P.=263° C.

The base was extracted and obtained with a yield of 40% (0.65 g).

Melting point M.P.=140° C.

IR spectrum (Nujol) ν=3500 to 2500 (max. to 3300 and 3150), 1615, 1590, 1550, 1515, 1410, 1170, 935, 830, 715 cm$^{-1}$.

EXAMPLE 3

3-(3-pyridyl)-4-methyl-5-methoxy-pyrazole

The process of Example 1 was repeated using 3-(3-pyridyl)-4-methyl-5-pyrazolone in order to obtain the desired product with a yield of 45%.

Melting point M.P.=134° C.

IR spectrum (Nujol) ν=3175, 1510, 1415, 1170, 1020 cm$^{-1}$.

HYDROCHLORIDE

Melting point M.P.=212°–214° C.

EXAMPLE 4

3-(2-pyridyl)-4-methyl-5-methoxy-pyrazole

The process of Example 1 was repeated using 3-(2-pyridyl)-4-methyl-5-pyrazole in order to obtain the desired product with a yield of 40%.

HYDROCHLORIDE

Melting point M.P.=156°–158° C.

EXAMPLE 5

3-(4-pyridyl)-4-benzyl-5-methoxy-pyrazole 0.8 g of diazomethane were reacted with 3.6 g of 3-(4-pyridyl)-4-benzyl-5-pyrazolone using the technique described in Example 1, in a mixture of tetrahydrofuran and methanol, for 24 hours.

After evaporation of the solvent, extraction with methylene chloride, washing and trituration in diisopropyl ether, 2.2 g (yield 60%) of 3-(4-pyridyl)-4-benzyl-5- methoxy-pyrazole crystals were obtained which were purified by precipitation of the hydrochloride in isopropanol.

IR spectrum (Nujol) $v = 3380, 3160, 1635, 1605, 1580, 1505, 1490$ cm$^{-1}$.

HYDROCHLORIDE

Melting point M.P. = 186° C. (dec.)

EXAMPLE 6

3-(4-pyridyl)-4-methyl-5-ethoxy-pyrazole 5.3 g of 3-pyridyl-4-methyl-5-pyrazolone were placed under agitation in 120 ml of tetrahydrofuran, 8.6 g of triphenylphosphine and 1.8 ml of ethanol. The mixture was cooled on an ice bath to 2° C. and 5.2 ml of ethyl azodicarboxylate in solution in 20 ml of tetrahydrofuran was added dropwise. This mixture was allowed to react for 4 hours at room temperature.

The pyrazolone precipitate which had not reacted was removed by filtration. The tetrahydrofuran was evaporated until the product was dry and the residue was dissolved with a solution of hydrochloric acid. After washing with methylene chloride, the 3-(4-pyridyl)-4-methyl-5-ethoxy pyrazole hydrochloride obtained was recrystallized in methanol, then transformed into the corresponding base. In this manner 3.4 g of product (yield 55%) was obtained.

Melting point M.P. = 154°–156° C.

IR spectrum (Nujol) $v = 3000$ to $3400, 1615, 1590, 1550, 1510, 1355, 1170, 1040, 820, 715, 710$ cm$^{-1}$.

The experiments carried out on the 3-pyridyl-5-alkoxy pyrazole type derivatives in accordance with the invention have revealed interesting pharmacological properties, in particular inotropic activity, suggesting their use in human and veterinary medicine as cardiotonic medications to be envisaged.

The cardiac toxicity of the derivatives of general formula (I) is low, and it can for example be noted that in the test on the isolated guinea pig auricle, for a product dose of $3 \times 10^{-4}$ g/ml, no disorder in cardiac contraction was observed.

Inotropic activity was shown on the isolated guinea pig auricle under the following experimental conditions: the survival liquid was composed of a carbogene Tyrode solution (95% $O_2$ + 5% $CO_2$) thermostated at 30° C., the initial tension placed on the auricles was 0.5 g, the volume of substance to be tested added to the bath was 0.5 ml, and the volume of the organ bath was 40 ml; the stabilization time of the organ was 1 hour. The force and frequency of contraction were continuously recorded.

By way of example the 3-(4-pyridyl)-4-methyl-5-methoxy pyrazole described in Example 2 provided an increase of 120% in the force of maximum contraction under the conditions detailed above. This maximum was reached in 3 minutes and an increase of 25% in the force of contraction still subsisted after 60 minutes.

These results show that the derivatives in accordance with the invention of general formula (I) can be used in medecine, more particularly for the treatment of cardiac deficiency.

The derivatives of general formula (I) and their pharmaceutically acceptable salts can be administered in conventional forms, the active constituent being diluted in an appropriately selected pharmaceutically acceptable carrier, for example, in the form of tablets, capsules, lozenges, suppositories, injectable solutions or syrups.

By way of example, tablets can be prepared by mixing the derivative of general formula (I) or one of its salts, with one or several solid diluents, such as lactose, mannitol, starch, polyvinylpyrrolidone, magnesium stearate, talc, etc., Where necessary, the tablets may comprise several layers superposed around a nucleus, in accordance with conventional techniques, in order to ensure progressive release or a delayed effect of the active ingredient. The coating may, for example, be composed of one or several layers of polyvinyl acetate, carboxymethylcellulose or cellulose acetophthalate.

The derivative of the invention may also be administered in the form of a syrup or drinkable solution obtained by dissolving the derivative of formula (I), as necessary in the form of a pharmaceutically acceptable salt, in water or glycerol, for example, and, as necessary, adding a conventional additive such as a sweetener and an antioxidant.

Injectable solutions can be prepared using well-known techniques and can be composed, for example, of a solution containing a derivative of formula (I) or one of its pharmaceutically acceptable salts, dissolved in bidistilled water, a hydroalcoholic solution, propylene glycol, etc., or a mixture of such solvents. Where necessary, an appropriate additive such as a preservative may be added.

An effective dosage amount of active compound can easily be determined by a clinician upon consideration of all criteria such as the route of administration, the particular compound used, the condition of the patient, the duration of the treatment and utilizing the best judgment of the clinician. Daily dosage can be 1 to 30 mg/kg.

While the invention has been described in detail and with reference to specific embodiments thereof, it will be apparent to one skilled in the art that various changes and modifications can be made therein without departing from the spirit and scope thereof.

What is claimed is:

1. A 3-pyridyl-5-alkoxy-pyrazole derivative represented by the following formula (I):

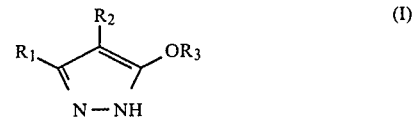

wherein $R_1$ represents a 4-pyridyl, 3-pyridyl or 2-pyridyl group which is unsubstituted or which may be substituted with one or two lower alkyl groups; $R_2$ represents a hydrogen atom or a lower alkyl group; and $R_3$ represents a lower alkyl group, a phenyl group or an benzyl group; or a pharmaceutically acceptable acid addition salt thereof.

2. The derivative of claim 1, wherein $R_1$ is a 4-pyridyl, 3-pyridyl or 2-pyridyl group.

3. The derivative of claim 1, wherein $R_2$ is a hydrogen atom or a methyl group.

4. The derivative of claim 1, wherein $R_3$ is a methyl group, an ethyl group, an isopropyl group, a phenyl group or a benzyl group.

5. The derivative of claim 1, wherein said derivative is 3-(4-pyridyl)-4-methyl-5-methoxy-pyrazole or a pharmaceutically acceptable salt thereof.

6. A pharmaceutical composition for use as a cardiotonic medication comprising a therapeutically effective amount of a 3-pyridyl-5-alkoxy-pyrazole derivative represented by the following formula (I):

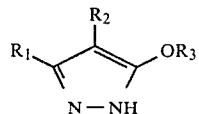

wherein $R_1$ represents a 4-pyridyl, 3-pyridyl or 2-pyridyl group which is unsubstituted or which may be substituted with one or two lower alkyl groups; $R_2$ represents a hydrogen atom or a lower alkyl group; and $R_3$ represents a lower alkyl group, a phenyl group or an benzyl group; or a pharmaceutically acceptable salt thereof as an active ingredient, and a pharmaceutically acceptable excipient.

7. A pharmaceutical composition for use as a cardiotonic medication comprising a therapeutically effective amount of a 3-pyridyl-5-alkoxy-pyrazole derivative represented by the following formula (I):

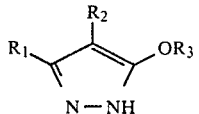

wherein $R_1$ represents a 4-pyridyl, 3-pyridyl or 2-pyridyl group; $R_2$ represents a hydrogen atom or a lower alkyl group; and $R_3$ represents a lower alkyl group, a phenyl group or an benzyl group; or a pharmaceutically acceptable salt thereof as an active ingredient, and a pharmaceutically acceptable excipient.

8. A pharmaceutical composition for use as a cardiotonic medication comprising a therapeutically effective amount of a 3-pyridyl-5-alkoxy-pyrazole derivative represented by the following formula (I):

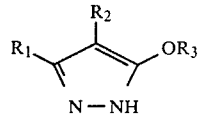

wherein $R_1$ represents a 4-pyridyl, 3-pyridyl or 2-pyridyl group which is unsubstituted or which may be substituted with one or two lower alkyl groups; $R_2$ represents a hydrogen atom or a methyl group; and $R_3$ represents a lower alkyl group, a phenyl group or an benzyl group; or a pharmaceutically acceptable salt thereof as an active ingredient, and a pharmaceutically acceptable excipient.

9. A pharmaceutical composition for use as a cardiotonic medication comprising a therapeutically effective amount of a 3-pyridyl-5-alkoxy-pyrazole derivative represented by the following formula (I):

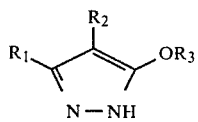

wherein $R_1$ represents a 4-pyridyl, 3-pyridyl or 2-pyridyl group which is unsubstituted or which may be substituted with one or two lower alkyl groups; $R_2$ represents a hydrogen atom or a lower alkyl group; and $R_3$ represents is a methyl group, an ethyl group, an isopropyl group, a phenyl group or a benzyl group; or a pharmaceutically acceptable salt thereof as an active ingredient, and a pharmaceutically acceptable excipient.

10. A pharmaceutical composition for use as a cardiotonic medication comprising a therapeutically effective amount of 3-(4-pyridyl)-4-methyl-5-methoxy-pyrazole or a pharmaceutically acceptable salt thereof as an active ingredient, and a pharmaceutically acceptable excipient.

* * * * *